(12) United States Patent
Roeder (10) Patent No.: US 9,278,018 B2
(45) Date of Patent: Mar. 8, 2016

(54) CIRCUMFERENTIAL TRIGGER WIRE FOR DEPLOYING AN ENDOLUMINAL PROSTHESIS

(71) Applicant: Cook Medical Technologies LLC, Bloomington, IN (US)

(72) Inventor: Blayne A. Roeder, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 390 days.

(21) Appl. No.: 13/713,517

(22) Filed: Dec. 13, 2012

(65) Prior Publication Data

US 2013/0158646 A1 Jun. 20, 2013

Related U.S. Application Data (60) Provisional application No. 61/570,439, filed on Dec. 14, 2011.

(51) Int. Cl.
*A61F 2/06* (2013.01)
*A61F 2/95* (2013.01)
*A61F 2/966* (2013.01)

(52) U.S. Cl.
CPC . *A61F 2/95* (2013.01); *A61F 2/966* (2013.01); *A61F 2002/9665* (2013.01)

(58) Field of Classification Search
CPC ... A61F 2/95; A61F 2/966; A61F 2002/9505; A61F 2002/9511; A61F 2002/9665
See application file for complete search history.

(56) References Cited

U.S. PATENT DOCUMENTS

| | | | | |
|---|---|---|---|---|
| 4,878,906 | A | * 11/1989 | Lindemann | A61F 2/91 606/108 |
| 4,913,141 | A | * 4/1990 | Hillstead | 623/1.11 |
| 5,843,158 | A | 12/1998 | Lenker et al. | 623/1.11 |
| 6,562,064 | B1 | 5/2003 | deBeer | 623/1.11 |
| 6,964,677 | B2 | 11/2005 | Osypka | 623/1.11 |
| 7,160,318 | B2 | 1/2007 | Greenberg et al. | 623/1.13 |
| 7,611,528 | B2 | 11/2009 | Goodson, IV et al. | 623/1.11 |
| 7,803,177 | B2 | 9/2010 | Hartley et al. | 623/1.11 |

(Continued)

FOREIGN PATENT DOCUMENTS

| WO | WO 01/74270 A2 | 10/2001 |
|---|---|---|
| WO | WO 2006/037086 A1 | 4/2006 |

OTHER PUBLICATIONS

Extended European Search Report dated Apr. 4, 2013, pp. 1-7, European Patent Application No. 12197088.3, European Patent Office, The Netherlands.

*Primary Examiner* — David C Eastwood
(74) *Attorney, Agent, or Firm* — Brinks Gilson & Lione (57) ABSTRACT

A deployment device for deploying an expandable endoluminal prosthesis within a body vessel may include an elongate member extending longitudinally along at least a portion of a length of the deployment device. The deployment device may include at least one engagement member coupled to the elongate member and extending outwardly from the elongate member. The deployment device may include a circumferential trigger wire extending at least partially circumferentially around the elongate member and removably received between the engagement member and the elongate member. The circumferential trigger wire may be manipulatable from a distal end of the deployment device, whereby the circumferential trigger wire is removable from between the engagement member and the elongate member.

18 Claims, 8 Drawing Sheets

(56) References Cited

U.S. PATENT DOCUMENTS

| | | | |
|---|---|---|---|
| 7,909,863 B2 | 3/2011 | Hartley et al. | 623/1.13 |
| 2001/0041925 A1* | 11/2001 | Konya et al. | 623/1.11 |
| 2002/0007208 A1* | 1/2002 | Strecker | 623/1.12 |
| 2003/0233140 A1* | 12/2003 | Hartley et al. | 623/1.11 |
| 2004/0073289 A1* | 4/2004 | Hartley | 623/1.13 |
| 2004/0220655 A1* | 11/2004 | Swanson et al. | 623/1.11 |
| 2005/0085890 A1* | 4/2005 | Rasmussen et al. | 623/1.11 |
| 2005/0090887 A1* | 4/2005 | Pryor | 623/1.11 |
| 2005/0107862 A1* | 5/2005 | Ohlenschlaeger | 623/1.11 |
| 2005/0137701 A1* | 6/2005 | Salahieh et al. | 623/2.38 |
| 2006/0142836 A1* | 6/2006 | Hartley et al. | 623/1.11 |
| 2007/0100427 A1* | 5/2007 | Perouse | 623/1.11 |
| 2007/0233223 A1* | 10/2007 | Styrc | A61F 2/2439 623/1.11 |
| 2008/0027529 A1 | 1/2008 | Hartley et al. | |
| 2008/0140178 A1* | 6/2008 | Rasmussen et al. | 623/1.11 |
| 2009/0082842 A1* | 3/2009 | Glynn | 623/1.11 |
| 2009/0099640 A1* | 4/2009 | Weng | 623/1.11 |
| 2009/0171431 A1* | 7/2009 | Swanson et al. | 623/1.11 |
| 2009/0204202 A1* | 8/2009 | Dierking et al. | 623/1.16 |
| 2009/0259291 A1* | 10/2009 | Kolbel et al. | 623/1.13 |
| 2010/0010617 A1* | 1/2010 | Goodson IV et al. | 623/1.11 |
| 2010/0168838 A1* | 7/2010 | Hartley et al. | 623/1.11 |
| 2010/0211052 A1* | 8/2010 | Brown | A61F 2/95 606/1 |
| 2010/0249896 A1* | 9/2010 | Sugimoto et al. | 623/1.11 |
| 2010/0286768 A1* | 11/2010 | Alkhatib | A61F 2/2436 623/2.11 |
| 2010/0324655 A1* | 12/2010 | Styrc | A61F 2/962 623/1.15 |
| 2011/0178588 A1 | 7/2011 | Haselby | 623/1.11 |
| 2011/0190865 A1* | 8/2011 | McHugo et al. | 623/1.11 |
| 2011/0288624 A1* | 11/2011 | Roeder et al. | 623/1.11 |
| 2012/0010696 A1* | 1/2012 | Greenberg et al. | 623/1.12 |
| 2012/0277848 A1* | 11/2012 | Roeder et al. | 623/1.13 |
| 2013/0245743 A1* | 9/2013 | Norris | 623/1.11 |

* cited by examiner

CIRCUMFERENTIAL TRIGGER WIRE FOR DEPLOYING AN ENDOLUMINAL PROSTHESIS

CROSS-REFERENCE TO RELATED APPLICATIONS

This application claims priority and the benefit of provisional U.S. Patent Application Ser. No. 61/570,439, filed Dec. 14, 2011, which is incorporated herein by reference in its entirety.

TECHNICAL FIELD

This disclosure relates generally to apparatus and methods for treating medical conditions. More specifically, this disclosure relates to apparatus and methods for deploying endoluminal prostheses in body vessels to treat those medical conditions.

BACKGROUND

Endoluminal prostheses may be inserted into a body lumen such as an anatomical vessel or duct for various purposes. Prostheses may maintain or restore patency in a formerly blocked or constricted passageway, for example, following a balloon angioplasty procedure. Other prostheses may be used for different procedures. For example, a prosthesis may include one or more stents placed in or about a graft, and the stents may hold the graft in an open configuration to treat an aneurysm. Additionally, stents coupled to one or both ends of a graft may extend proximally or distally away from the graft to engage a healthy portion of a vessel wall away from a diseased portion of an aneurysm to provide endovascular graft fixation.

Stents may be either self-expanding or balloon-expandable. In some examples, stents can have characteristics of both self-expanding and balloon-expandable stents. Self-expanding stents may be delivered to a target site in a compressed configuration and subsequently expanded by removing a delivery sheath, removing trigger wires, and/or releasing diameter reducing ties. A self-expanding stent expands primarily based on its own expansive force without the need for further mechanical expansion. A stent may be made of a shape-memory alloy such as nitinol. The shape-memory alloy may be employed to cause the stent to return to a predetermined configuration upon removal of the sheath or other device maintaining the stent in its predeployment configuration.

Deployment devices are used to deploy prostheses, particularly those including self-expanding stents, within various body lumens. In some deployment devices, trigger wires are used to restrain a prosthesis in a particular position on the deployment device or to restrain one or more self-expanding stents of the prosthesis in a compressed state. The trigger wires may releasably couple the proximal and/or distal ends of the prosthesis to the deployment device. Typically, one or more trigger wires are looped through a portion of a stent near a vertex of the stent. For example, trigger wires may be used to restrain a "Z-stent" or Gianturco stent having a series of substantially straight segments interconnected by a series of bent segments. The trigger wires may be disposed through, and pull upon, the bent segments to pull the stent closely against the deployment device.

In the region of the deployment device in which the prosthesis is carried, trigger wires can foul or catch with stent components on the prosthesis, particularly when the deployment device is bent to pass through convolutions in the anatomical vessel or duct. This may cause inaccurate deployment or even jamming or breakage of the trigger wire.

Trigger wires also may be used in conjunction with different stent designs such as cannula-cut stents having relatively acute or pointed bends. The designs of cannula-cut stents may facilitate compression of the stents to a relatively small delivery profile due to the tight bends of the apices. With such stents, the trigger wires may be looped around one or more vertices formed at the proximal and/or distal apices, e.g., a location where an individual apex splits into two separate strut segments.

If trigger wires are threaded through the vertices of such cannula-cut stents, the trigger wires may become crimped at the vertices during compression of the stents to a reduced diameter delivery profile. If the trigger wires are crimped between the strut segments, the trigger wires and/or strut segments may become damaged. Furthermore, when compressing cannula-cut stents having relatively acute bends to a significantly reduced radial profile, barbs disposed near the apices of the stents may become entangled with the stent struts and/or the trigger wires.

Typically, multiple trigger wires are threaded through multiple vertices of a stent to restrain the end of the stent in the reduced diameter delivery profile. Additional trigger wires may be added to more securely restrain the stent. However, such additional trigger wires may increase the retraction force that is required to release the stent. Such additional trigger wires also may increase the likelihood of one or more of the trigger wires becoming entangled with portions of the stent such as barbs.

In view of the above, it would be desirable to provide an apparatus configured to release a stent with a reduced retraction force while also reducing the likelihood of entanglement and damage to the trigger wires and stent struts.

SUMMARY

The present embodiments provide an endoluminal prosthesis for implantation within a human or animal body for repair of damaged vessels, ducts, or other physiological pathways and systems and method for delivering such an endoluminal prosthesis.

In one example, a deployment device for deploying an expandable endoluminal prosthesis within a body vessel may include an elongate member extending longitudinally along at least a portion of a length of the deployment device. The deployment device may include at least one engagement member coupled to the elongate member and extending outwardly from the elongate member. The deployment device may include a circumferential trigger wire extending at least partially circumferentially around the elongate member and removably received between the engagement member and the elongate member. The circumferential trigger wire may be manipulatable from a distal end of the deployment device, whereby the circumferential trigger wire is removable from between the engagement member and the elongate member.

In another example, a system may include a deployment device and an expandable endoluminal prosthesis positioned on the deployment device. The deployment device may include a tubular trigger wire guide. The tubular trigger wire guide may include at least one axial trigger wire aperture in the trigger wire guide and at least one circumferential trigger wire aperture in the trigger wire guide. The system may include at least one axial trigger wire received within the trigger wire guide. The axial trigger wire may extend through the axial trigger wire aperture and exit the trigger wire guide.

The system may include a circumferential trigger wire received within the trigger wire guide. The circumferential trigger wire may extend through the circumferential trigger wire aperture and exit the trigger wire guide and at least partially encircle the prosthesis. The circumferential trigger wire may be engaged by the axial trigger wire and restrain at least a portion of the prosthesis in a compressed configuration.

In another example, a method of deploying an endoluminal prosthesis may include providing a deployment device including a tubular trigger wire guide. The trigger wire guide may include at least one axial trigger wire aperture in the trigger wire guide. An axial trigger wire may be received within the trigger wire guide and extend through the axial trigger wire aperture such that a curve of the axial trigger wire is disposed external of the trigger wire guide. A circumferential trigger wire may at least partially encircle the trigger wire guide. The method may include manipulating the circumferential trigger wire from a distal end of the deployment device, and sliding the circumferential trigger wire out of engagement between the curve of the axial trigger wire and an outer surface of the trigger wire guide.

Other systems, methods, features, and advantages of the invention will be, or will become, apparent to one with skill in the art upon examination of the following figures and detailed description. It is intended that all such additional systems, methods, features, and advantages be within the scope of the invention, and be encompassed by the following claims.

DETAILED DESCRIPTION OF THE DRAWINGS AND THE PRESENTLY PREFERRED EMBODIMENTS

The present disclosure relates to apparatus and methods for deploying endoluminal prostheses in body vessels to treat various medical conditions.

In the present disclosure, the term "proximal" refers to a direction that is generally closest to the heart during a medical procedure, while the term "distal" refers to a direction that is farthest from the heart during a medical procedure.

Figure 1:
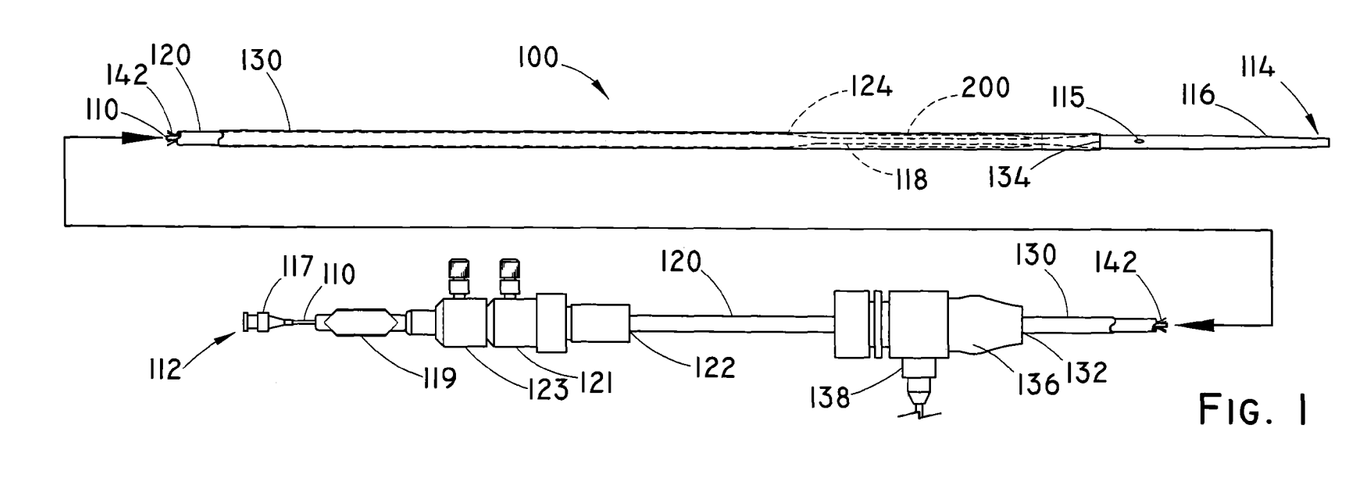
FIG. 1 depicts one embodiment of a deployment device for deploying an endoluminal prosthesis.
Figure 2:
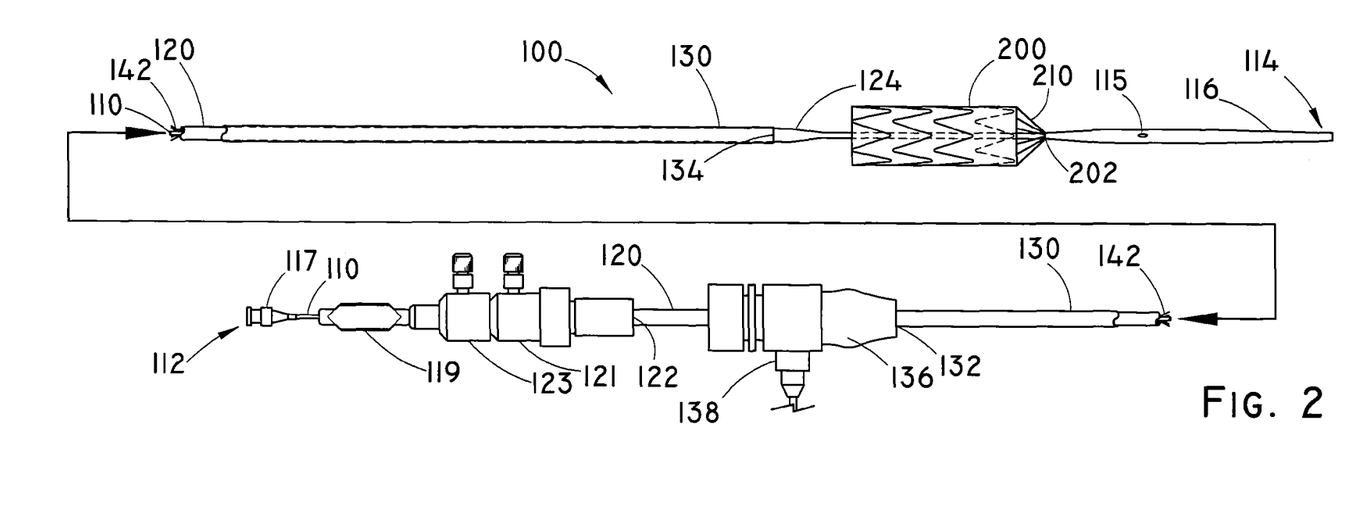
FIG. 2 depicts the deployment device of FIG. 1 with a sheath retracted to expose an endoluminal prosthesis loaded on the deployment device.

FIGS. 1-2 show one embodiment of a deployment device 100 for deploying an endoluminal prosthesis 200. The deployment device 100 may include a guide wire catheter 110. The guide wire catheter 110 may be configured as an elongate tubular member having a distal end 112, a proximal end 114, and a lumen extending longitudinally between the distal and proximal ends of the guide wire catheter. In use, the distal end 112 may be adapted to remain outside of the body of the patient while the proximal end 114 may be adapted for insertion into a body vessel within the body of the patient. To that end, a nose cone dilator 116 may be positioned at the proximal end 114 of the guide wire catheter 110. The nose cone dilator 116 may be configured as an elongate tapered extension to aid in advancing the proximal end of the deployment device 100 within the body vessel. The nose cone dilator 116 may include a lumen configured to receive a guide wire. The guide wire catheter 110 may include a connector 117 (e.g., a Luer Lock hub) disposed at the distal end 112 of the guide wire catheter. The connector 117 may be configured to enable the introduction of liquids (e.g., contrast media or therapeutic agents) during a deployment procedure. In one example, an angiographic contrast fluid may be introduced into the connector 117. The contrast fluid may travel through the guide wire catheter 110 to the nose cone dilator 116 where the contrast fluid may be ejected from one or more side ports 115 in the nose cone dilator.

A pusher catheter 120 may surround at least a portion of the guide wire catheter 110. The pusher catheter 120 may be configured as an elongate tubular member having a distal end 122, a proximal end 124, and a lumen extending longitudinally between the distal and proximal ends of the pusher catheter. The guide wire catheter 110 may be movable longitudinally and/or rotationally with respect to the pusher catheter 120. In one example, the guide wire catheter 110 may be moved proximally or distally within the pusher catheter 120 to move the nose cone dilator 116 relative to the pusher catheter. A pin vise 119 may be positioned near the distal end 112 of the guide wire catheter 110 and configured to lock the guide wire catheter in place relative to the pusher catheter 120.

A sheath 130 may surround at least a portion of the pusher catheter 120. The sheath 130 may be configured as an elongate tubular member having a distal end 132, a proximal end 134, and a lumen extending longitudinally between the distal and proximal ends of the sheath. A sheath hub 136 may be positioned at the distal end 132 of the sheath 130. The sheath hub 136 may include a side tube 138. The side tube 138 may include a connector (not shown) configured to enable the introduction of liquids between the sheath 130 and the pusher catheter 120.

A recess 118 may be formed between the nose cone dilator 116 and the proximal end 124 of the pusher catheter 120 as shown in FIGS. 1-2. In other embodiments, a portion of the pusher catheter 120 may be configured as a trigger wire guide as further described below. In these embodiments, the recess 118 may surround a segment of the pusher catheter 120 having a smaller diameter than the remainder of the pusher catheter. The prosthesis 200 may be received in the recess 118 for delivery to a desired location within a body vessel. The prosthesis 200 may be restrained in a compressed delivery configuration within the lumen of the sheath 130. Upon retraction of the sheath 130 to expose the prosthesis 200, the prosthesis may at least partially expand to an expanded configuration. A portion of the prosthesis 200 may be restrained in the compressed configuration even after retraction of the sheath 130. For example, a proximal end 202 of the prosthesis 200 may be restrained in the compressed configuration by a trigger wire system as further described below.

Figures 9, 10, 11:
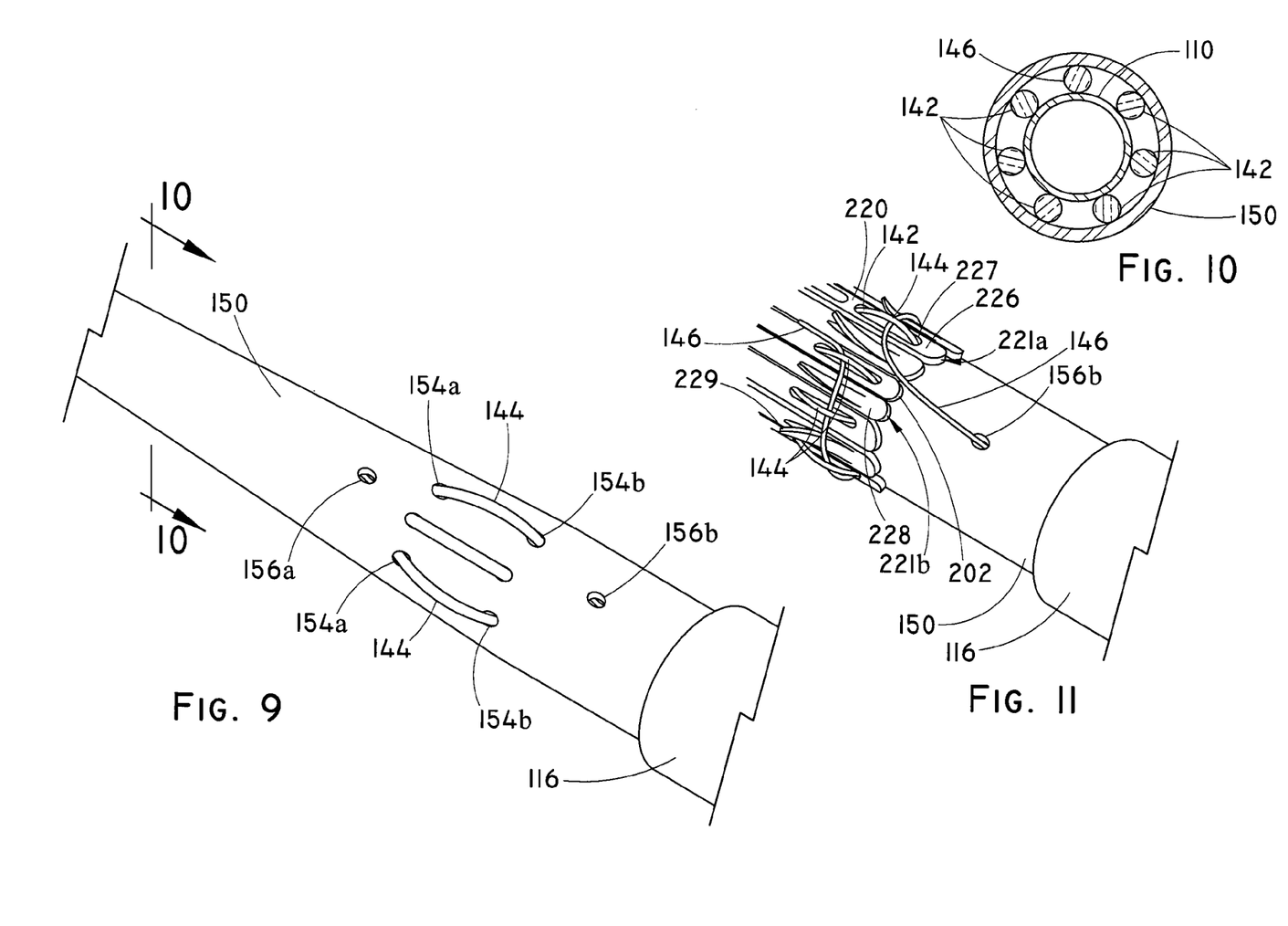
FIG. 9 depicts an intermediate portion of one embodiment of a deployment device with axial trigger wires loaded therein.
FIG. 10 is a transverse cross sectional view of the deployment device taken along line 10-10 of FIG. 9.
FIG. 11 depicts an intermediate portion of the deployment device of FIG. 9 with a prosthesis restrained by a circumferential trigger wire.

The deployment device 100 may include a trigger wire system configured to restrain at least a portion of the prosthesis 200 in the compressed configuration. The trigger wire system may include one or more axial trigger wires 142 extending generally longitudinally along at least a portion of the length of the deployment device 100. In one example, the trigger wire system may include four axial trigger wires as shown in FIGS. 1-4. In another example, the trigger wire system may include six axial trigger wires as shown in FIGS. 9-11. In other examples, the trigger wire system may include any number of axial trigger wires. The axial trigger wires 142 may be attached to an axial trigger wire release mechanism 121, which may be positioned near the distal end 122 of the pusher catheter 120. The axial trigger wires 142 may extend proximally through the deployment device 100 in the annular space between the pusher catheter 120 and the guide wire catheter 110. The axial trigger wires 142 may exit the proximal end 124 of the pusher catheter and extend into the recess 118. The axial trigger wires 142 may engage the prosthesis 200 to restrain at least a portion of the prosthesis in the compressed configuration as further described below. Alternatively, or additionally, the axial trigger wires 142 may engage a circumferential trigger wire 146 also as further described below. The proximal end of each axial trigger wire may be releasably received within the nose cone dilator 116 and/or the guide wire catheter 110 to maintain tension on the axial trigger wire to restrain the prosthesis 200. The nose cone dilator 116 and/or the guide wire catheter 110 may frictionally engage the received proximal end of the axial trigger wire 142 to maintain tension on the axial trigger wire. Alternatively, or additionally, the proximal end of the axial trigger wire 142 may be releasably attached to the nose cone dilator 116 and/or the guide wire catheter 110 by any suitable means including, for example, an adhesive or a mechanical attachment mechanism.

The trigger wire system may include at least one circumferential trigger wire 146 (see FIGS. 11-12) extending generally longitudinally along at least a portion of the length of the deployment device 100. The circumferential trigger wire 146 may be attached to a circumferential trigger wire release mechanism 123, which may be positioned near the distal end 122 of the pusher catheter 120. In one example, the circumferential trigger wire release mechanism 123 may be positioned just distal of the axial trigger wire release mechanism 121 as shown in FIGS. 1-2. A distal portion of the circumferential trigger wire 146 may extend proximally through the deployment device 100 in the annular space between the pusher catheter 120 and the guide wire catheter 110. The circumferential trigger wire 146 may exit the proximal end 124 of the pusher catheter and extend into the recess 118. A proximal portion of the circumferential trigger wire 146 may engage the prosthesis 200 to restrain at least a portion of the prosthesis in the compressed configuration as further described below. The proximal end of the circumferential trigger wire 146 may be releasably received within the nose cone dilator 116 and/or the guide wire catheter 110 to maintain tension on the circumferential trigger wire to restrain the prosthesis 200. The nose cone dilator 116 and/or the guide wire catheter 110 may frictionally engage the received proximal end of the circumferential trigger wire 146 to maintain tension on the circumferential trigger wire. Alternatively, or additionally, the proximal end of the circumferential trigger wire 146 may be releasably attached to the nose cone dilator 116 and/or the guide wire catheter 110 by any suitable means including, for example, an adhesive or a mechanical attachment mechanism.

Figure 3:
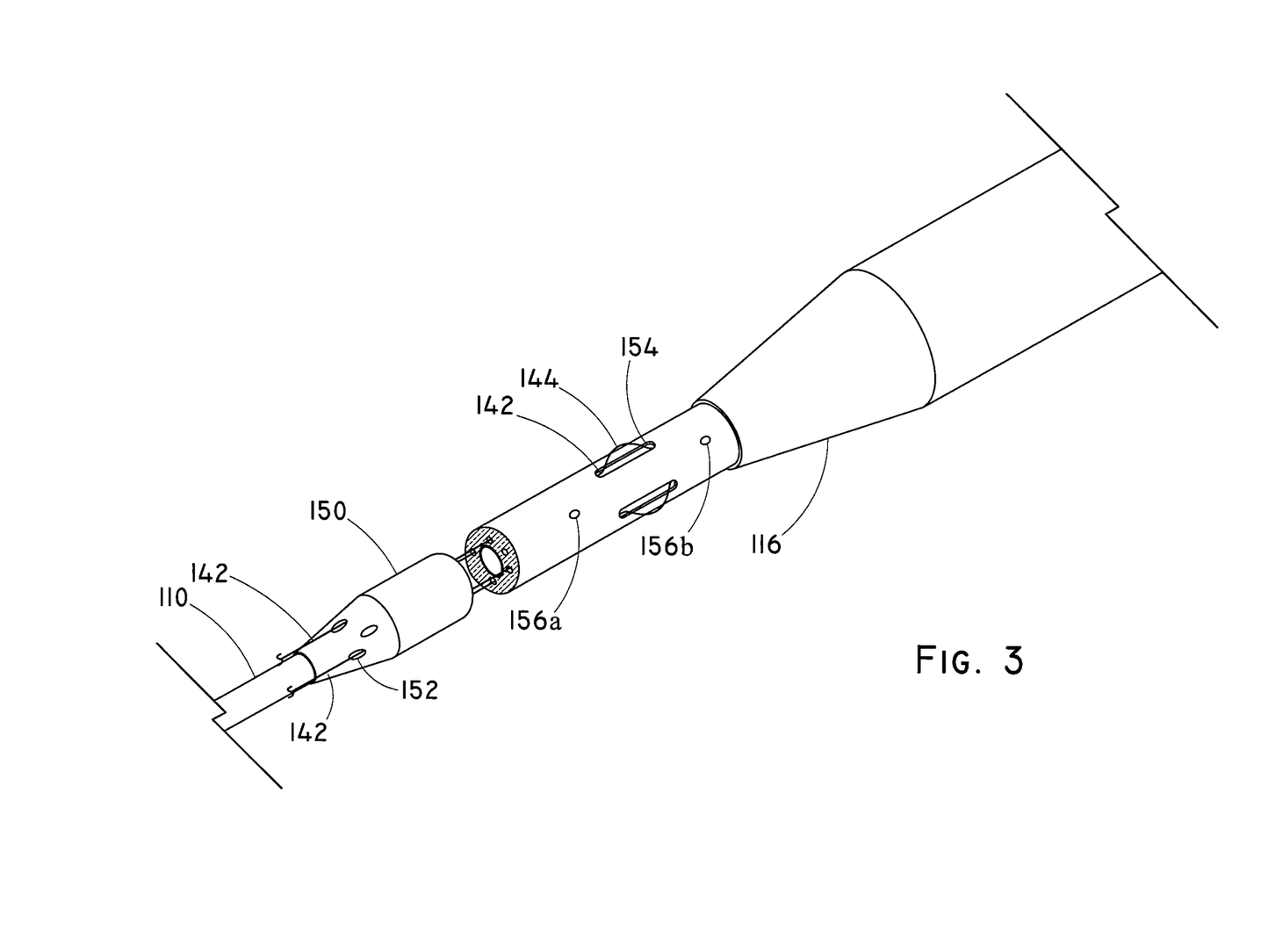
FIG. 3 depicts one embodiment of a trigger wire guide.

The deployment device 100 may include an elongate member such as, for example, a trigger wire guide 150 as shown in FIG. 3. The trigger wire guide 150 may surround a portion of the guide wire catheter 110 near the nose cone dilator 116. Inside the recess 118, the axial trigger wires 142 may enter a distal end of the trigger wire guide 150. The trigger wire guide 150 may have any suitable configuration including, for example, those described in U.S. Pat. No. 7,803,177 to Hartley et al., which is incorporated by reference herein in its entirety. In the example shown in FIG. 3, the trigger wire guide 150 may be configured as a tubular member surrounding at least a portion of the guide wire catheter 110. The trigger wire guide 150 may include one or more trigger wire lumens 152 extending longitudinally within the trigger wire guide. The trigger wire guide 150 may include one or more elongate apertures 154. Each elongate aperture 154 may extend through the outer wall of the trigger wire guide 150 to the corresponding trigger wire lumen 152. For example, the trigger wire guide 150 may include four trigger wire lumens 152 as shown in FIG. 3. An axial trigger wire 142 may be received within each trigger wire lumen 152. Each axial trigger wire 142 may extend proximally within the trigger wire lumen 152 to the corresponding elongate aperture 154.

An engagement member may be coupled to the elongate member and may extend outwardly from the elongate member. For example, at the elongate aperture 154, the axial trigger wire 142 may exit the trigger wire guide 150, extend further proximally, and reenter the trigger wire guide through the elongate aperture. In this manner, the portion of the axial trigger wire 142 external of the trigger wire guide 150 may form an engagement member configured as a curve 144. The curve 144 may be coupled to the trigger wire guide 150 by the engagement of the axial trigger wire 142 with the elongate aperture 154. The curve 144 may be configured to engage the prosthesis 200 and/or the circumferential trigger wire 146 as further described below.

Although the engagement member is generally described herein as the curve 144 formed by the axial trigger wire 142, the disclosure is not so limited. In other examples, an engagement member may be positioned near the nose cone dilator 116 to engage the circumferential trigger wire 146 as further described below. For example, opposite ends of a wire segment may be attached to the trigger wire guide 150, and an intermediate portion of the wire segment may form the engagement member. In this example, the wire segment may not be received within the trigger wire guide 150. Additionally, or alternatively, the wire segment may not extend to the distal end of the deployment device as described herein with reference to the axial trigger wire 142. In another example, a protrusion (e.g., a loop or eyelet) may extend from the trigger wire guide 150 to form the engagement member. The protrusion may be formed separately from or integrally with the trigger wire guide 150. The protrusion may include an opening to engage the circumferential trigger wire 146 as further described below. Such alterations are contemplated by and within the scope of this disclosure.

In any of the examples described herein, the trigger wire guide may include a pair of openings 154*a*, 154*b* in place of the elongate aperture 154 as described below with reference to FIGS. 9-12. In any of the examples described herein, an annular space may be formed between the trigger wire guide 150 and the guide wire catheter 110. The trigger wire lumens 152 may be omitted, and the axial guide wires 142 and/or the circumferential guide wire 146 may be received within the annular space, also as described below with reference to FIGS. 9-12. Such alternative embodiments are within the scope of this disclosure.

Figure 4:
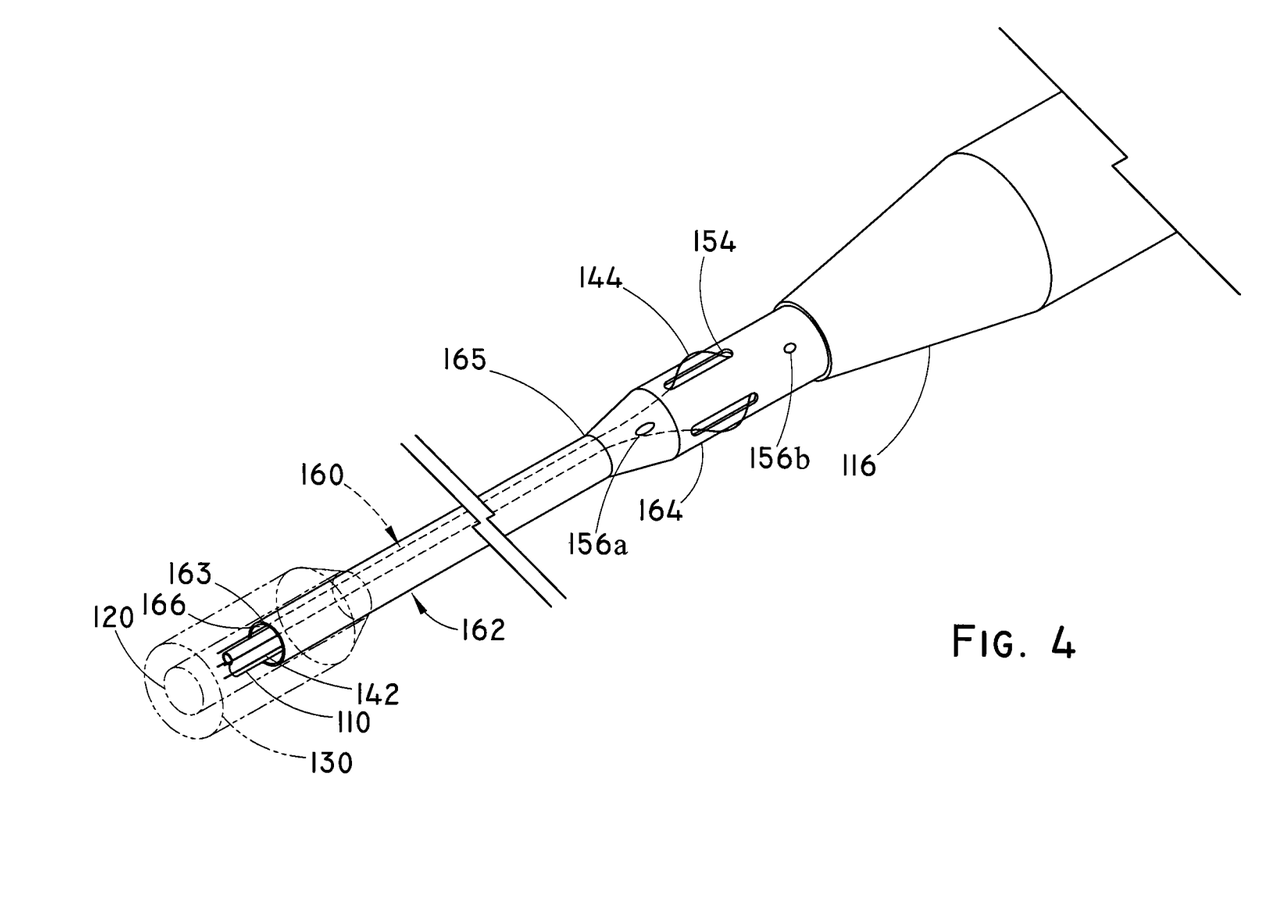
FIG. 4 depicts another embodiment of a trigger wire guide.

FIG. 4 shows an alternative example of a trigger wire guide 160. In any of the examples described herein, the trigger wire guide 160 (or various features thereof) may be used in place of or in addition to the trigger wire guide 150. In this example, the trigger wire guide 160 may include a tubular guide portion 162 and an enlarged engagement portion 164. The trigger wire guide 160 may surround the guide wire catheter 110 as described above with reference to the trigger wire guide 150. A distal end 163 of the tubular guide portion 162 may be positioned near the proximal end 124 of the pusher catheter 120. In one example, the distal end 163 of the tubular guide portion 162 may be received within the lumen of the pusher catheter 120. In another example, the trigger wire guide 160 and the pusher catheter 120 may be formed as a unitary tubular structure, and the tubular guide portion 162 may extend from the proximal end 124 of the pusher catheter. Positioning the distal end 163 of the trigger wire guide 160 near the proximal end 124 of the pusher catheter 120 may reduce the length of the axial trigger wires 142 and/or the circumferential trigger wire 146 that may be exposed within the recess 118 of the deployment device 100. This may reduce the potential for snagging or catching a trigger wire on a portion of the prosthesis 200 or the deployment device 100 during deployment of the prosthesis.

The enlarged engagement portion 164 of the trigger wire guide 160 may extend proximally from a proximal end 165 of the tubular guide portion 162. The enlarged engagement portion 164 may extend to the nose cone dilator 116. The tubular guide portion 162 may have a diameter that is smaller than the diameter of the enlarged engagement portion 164. The smaller diameter tubular guide portion 162 may span a majority of the length of the recess 118 so that the prosthesis 200 may be compressed around the tubular guide portion for delivery. The enlarged engagement portion 164 may be configured to engage the proximal end 202 of the prosthesis 200 as further described below.

An annular space 166 may be formed between the guide wire catheter 110 and the trigger wire guide 160. The axial trigger wires 142 and the circumferential trigger wire 146 may extend longitudinally along the deployment device 100 within the annular space 166. The enlarged engagement portion 164 of the trigger wire guide 160 may include one or more elongate apertures 154. The elongate apertures 154 may be configured generally as described above with reference to the trigger wire guide 150. Each elongate aperture 154 may be in communication with the annular space 166 between the guide wire catheter 110 and the trigger wire guide 160. The axial trigger wires 142 may pass through the elongate apertures 154 to form the curves 144 to engage the prosthesis 200 and/or the circumferential trigger wire 146. The circumferential trigger wire 146 may pass through circumferential trigger wire openings in the trigger wire guide 160 to engage the prosthesis 200 as further described below.

Figure 5:
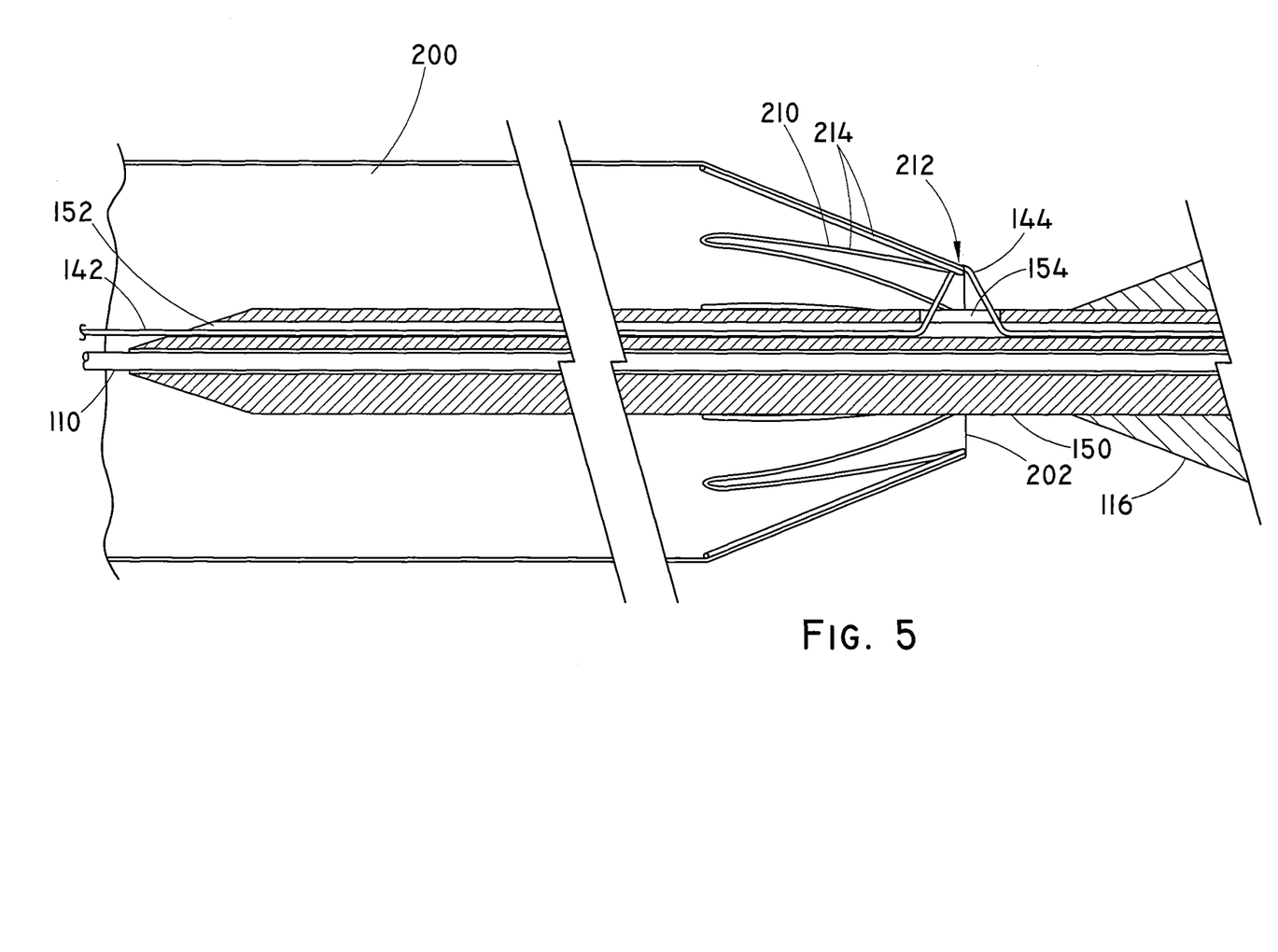
FIG. 5 is a partial longitudinal cross sectional view of the deployment device of FIG. 1 and a prosthesis restrained by an axial trigger wire.

FIG. 5 is a longitudinal cross sectional view of a proximal portion of the prosthesis 200 loaded on the deployment device 100. In the view shown in FIG. 5, the sheath 130 has been retracted to enable partial expansion of the prosthesis 200. The proximal end 202 of the prosthesis 200 may be restrained in the compressed configuration by the trigger wire system. For example, the axial trigger wire 142 may extend through the aperture 154 of the trigger wire guide 150 to form the curve 144 as described above. The curve 144 of the axial trigger wire 142 may engage a proximal stent 210 of the prosthesis 200. To that end, the axial trigger wire 142 may pass through a bend 212 interconnecting two adjacent struts 214 of the proximal stent 210. The axial trigger wire 142 may restrain the engaged bend 212 of the proximal stent 210 in close proximity to the trigger wire guide 150. Multiple axial trigger wires 142 may engage multiple bends 212 of the proximal stent 210 to restrain each engaged bend of the proximal stent in close proximity to the trigger wire guide 150. In this manner, the proximal end 202 of the prosthesis 210 may be restrained in the compressed configuration.

When the proximal stent 210 is compressed for delivery (e.g., when the prosthesis 200 is compressed within the sheath 130), the axial trigger wire 142 disposed through the bend 212 as shown in FIG. 5 may become pinched between the struts 214 of the stent. This may damage the stent 210 and/or the axial trigger wire 142. Thus, it may be beneficial for the axial trigger wires to engage the proximal stent of the prosthesis at locations other than the bends between adjacent struts of the stent.

Figure 6:
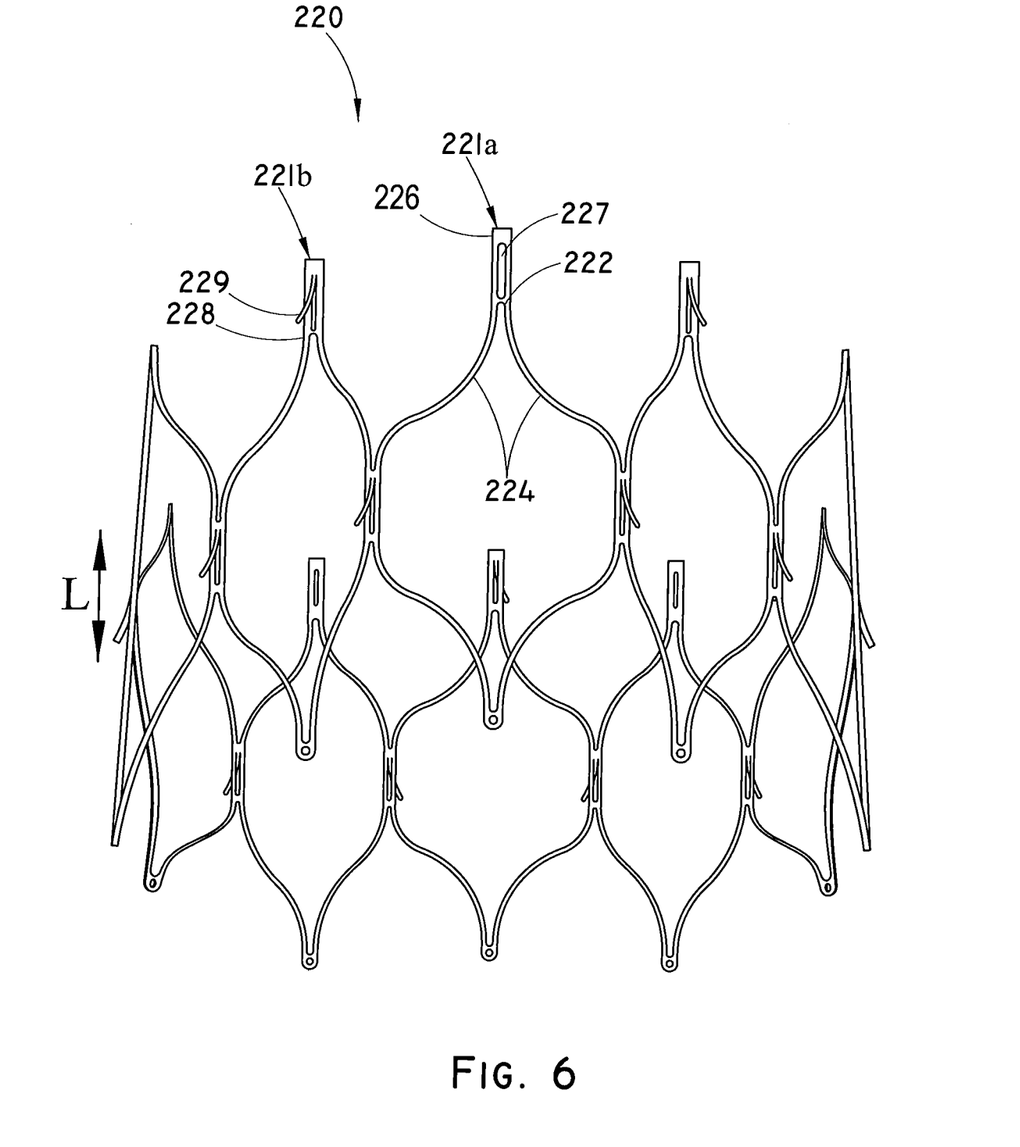
FIG. 6 depicts one embodiment of a stent.

U.S. Patent Application Pub. No. 2009/0204202 by Dierking et al., which is incorporated by reference herein in its entirety, describes stent designs which may be deployed using the deployment device 100 described herein. For example, FIG. 6 shows an alternative embodiment of a proximal stent 220. The prosthesis 200 may include the proximal stent 220 as opposed to the proximal stent 210 described above. Alternatively, the stent 210 may be modified to include one or more of the features of the stent 220 (e.g., the end regions 226) described below. The proximal stent 220 may include one or more first proximal apices 221a. Each first proximal apex 221a may include an end region 226 having an aperture 227 formed therein. The aperture 227 may be configured to receive an axial trigger wire 142 as further described below. The end region 226 may be positioned proximal of the bend 222 between two adjacent struts 224 of the stent 220 so that, upon compression of the prosthesis 200, the axial trigger wire 142 may not be pinched between the adjacent struts of the proximal stent 220. In other words, the end region 226 may be configured as an eyelet extending proximally from the bend 222 between two adjacent struts 224 to receive an axial trigger wire 142. The eyelet may remain open even after compression of the stent 220.

Additionally, or alternatively, the proximal stent 220 may include one or more second proximal apices 221b. Each second proximal apex 221b may include an end region 228 having an integral barb 229 formed therein. The barb 229 may be configured to engage a wall of a body vessel upon implantation of the prosthesis 200 to prevent migration of the prosthesis within the body vessel. The proximal stent 220 may include alternating first proximal apices and second proximal apices, as shown in FIG. 6, so that every other apex may be engaged by a trigger wire. In other examples, the proximal stent 220 may have any number of first proximal apices and second proximal apices. In one example, each apex of the first proximal stent 220 may be configured as a first proximal apex (i.e., each apex may include an end region 226 with an aperture 227).

Figure 7:
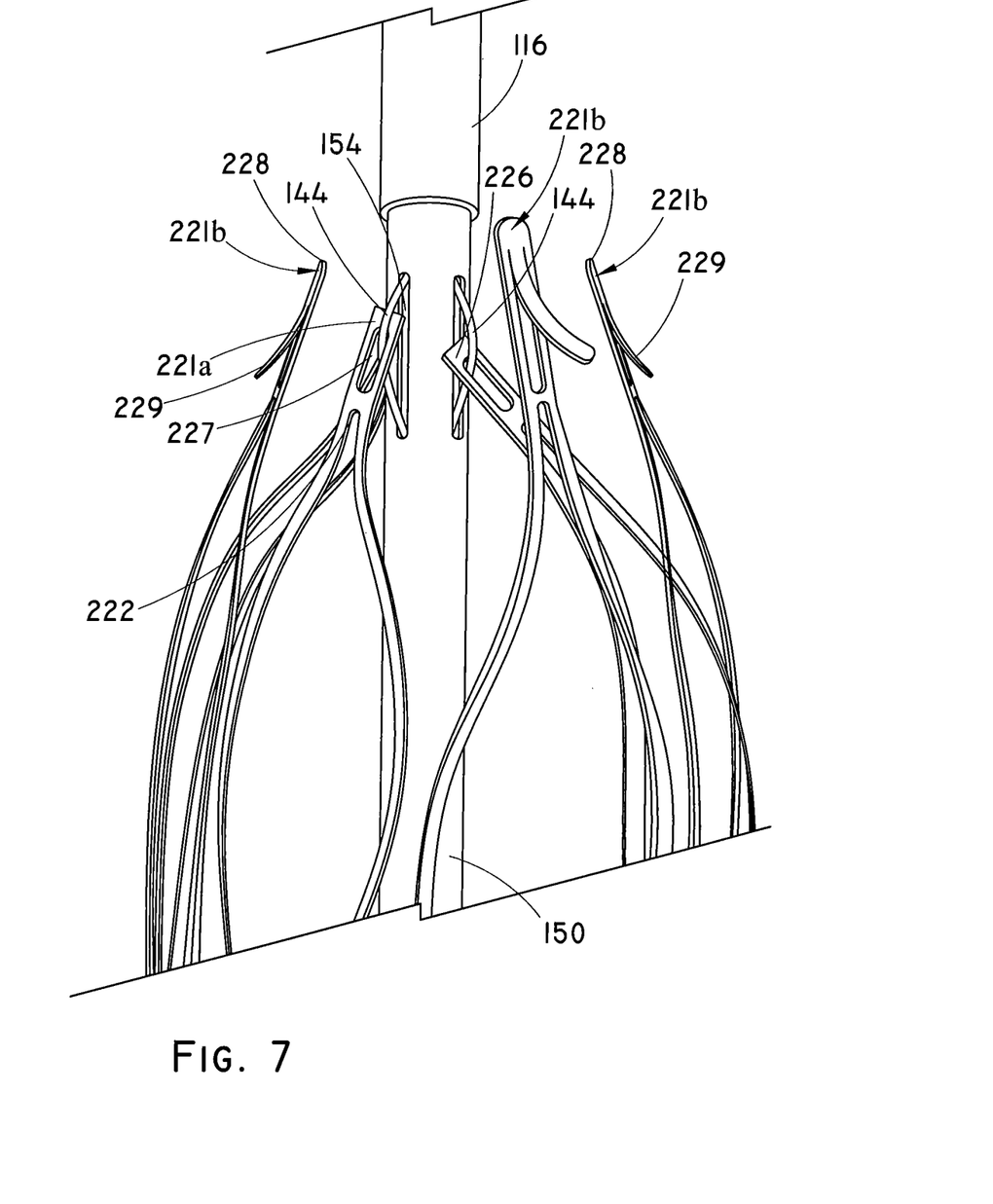
FIG. 7 depicts the stent of FIG. 6 with a proximal end of the stent partially restrained by a plurality of conventional axial trigger wires.
Figure 8:
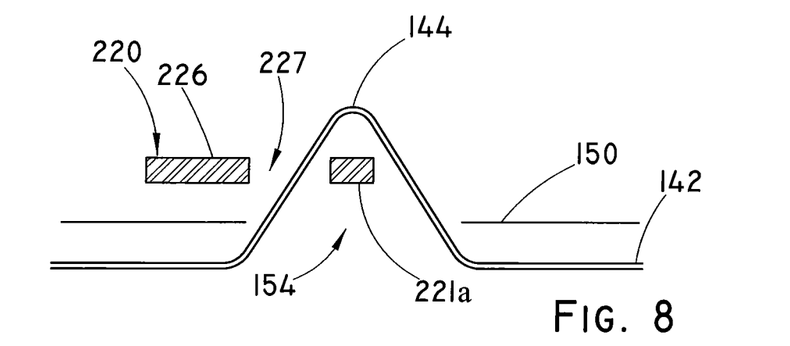
FIG. 8 is a partial longitudinal cross sectional view of the engagement between a conventional axial trigger wire and the stent as shown in FIG. 7.

FIG. 7 shows the proximal stent 220, with the proximal end of the proximal stent restrained in the partly compressed configuration by a conventional trigger wire system. FIG. 8 shows a partial longitudinal cross sectional view of one of the first proximal apices 221a engaged by an axial trigger wire 142 as shown in FIG. 7. The axial trigger wire 142 may exit the trigger wire guide 150 through the elongate aperture 154 as described above. The axial trigger wire 142 may pass through the aperture 227 of the proximal stent 220 of the prosthesis 200 and then reenter the trigger wire guide 150 through the elongate aperture 154. In this manner, the curve 144 of the axial trigger wire 142 may engage the end region 226 of the proximal stent 220 to restrain the end region in close proximity to the trigger wire guide 150.

One advantage of the trigger wire system shown in FIGS. 7-8 is that the axial trigger wires 142 may be disposed through the apertures 227 of the first proximal apices 221a as opposed to being disposed through the bends 222 of the proximal stent 220. This may reduce the probability that the axial trigger wires 142 and/or the struts 224 of the proximal stent 220 may become damaged upon compression of the prosthesis 200. In other words, because the apertures 227 may not be pinched closed upon compression of the prosthesis 200, pinching of the axial trigger wires 142 may be avoided.

As shown in FIG. 7, each of the first proximal apices 221a of the proximal stent 220 may be engaged by an axial trigger wire 142, while each of the second proximal apices 221b may remain unengaged by the axial trigger wires. Restraining the first proximal apices 221a in close proximity to the trigger wire guide 150 may indirectly restrain the adjacent second proximal apices 221b in a position that is closer to the trigger wire guide than in the expanded configuration. However, the second proximal apices 221b may remain farther from the trigger wire guide 150 than the first proximal apices 221a as shown in FIG. 7.

In one embodiment, the trigger wire system includes a circumferential trigger wire in addition to the axial trigger wires. The proximal portion of the circumferential trigger wire may extend at least partially circumferentially around the proximal stent of the prosthesis to restrain the proximal end of the prosthesis in the compressed configuration as further described below.

FIGS. 9-11 show an intermediate portion of one embodiment of the deployment device 100 having a circumferential trigger wire 146. The deployment device 100 may include the guide wire catheter 110 and the trigger wire guide 150 generally as described above with reference to FIGS. 1-5. FIG. 10 is a cross sectional view taken along line 10-10 of FIG. 9. At least one axial trigger wire 142 may extend longitudinally within the annular space between the guide wire catheter 110 and the trigger wire guide 150. For example, six axial trigger wires 142 may extend longitudinally within the trigger wire guide 150 as shown in FIGS. 9-10. Additionally, or alternatively, the distal portion of the circumferential trigger wire 146 may extend longitudinally within the trigger wire guide 150.

In this embodiment, the trigger wire guide 150 may include at least one pair of openings in place of the at least one elongate aperture 154. For example, the trigger wire guide 150 may include six pairs of openings as shown in FIGS. 9-11. Each pair of openings may include a first opening 154a and a second opening 154b. The first and second openings 154a, 154b may be aligned with one another with respect to a circumference of the trigger wire guide 150. The second opening 154b may be positioned longitudinally proximal of the first opening 154a. An axial trigger wire 142 may exit the trigger wire guide 150 through the first opening 154a, extend proximally external of the trigger wire guide, and reenter the trigger wire guide through the second opening 154b. In this manner, the curve 144 may be formed external of the trigger wire guide 150. Each axial trigger wire 142 may extend through a corresponding pair of openings. The pairs of openings may be aligned with one another with respect to the longitudinal axis of the trigger wire guide 150 and spaced from one another circumferentially around the trigger wire guide. Although the deployment device 100 shown in FIGS. 9-11 may include six axial trigger wires extending through six pairs of openings, any number of axial trigger wires (e.g., four axial trigger wires as described above with reference to FIGS. 3-5) extending through any number of pairs of openings may be used. Additionally, or alternatively, one or more elongate apertures may be used in place of one or more of the pairs of openings as described above with reference to FIGS. 3-5.

The trigger wire guide 150 may include a pair of circumferential trigger wire openings. The pair of circumferential trigger wire openings may include a first circumferential trigger wire opening 156a and a second circumferential trigger wire opening 156b. The first and second circumferential trigger wire openings 156a, 156b may be aligned with one another with respect to the circumference of the trigger wire guide 150. The second circumferential trigger wire opening 156b may be positioned longitudinally proximal of the first circumferential trigger wire opening 156a. The first circumferential trigger wire opening 156a may be positioned longitudinally distal of the first openings 154a, and the second circumferential trigger wire opening 156b may be positioned longitudinally proximal of the second openings 154b. The circumferential trigger wire 146 may exit the trigger wire guide 150 through the first circumferential trigger wire opening 156a, extend proximally and at least partially circumferentially around the trigger wire guide external of the trigger wire guide, and reenter the trigger wire guide through the second circumferential trigger wire opening 156b as shown in FIG. 11 and further described below.

FIG. 11 shows a proximal portion of the prosthesis 200 loaded on the deployment device 100. The prosthesis 200 may include a series of first proximal apices 221a and a series of second proximal apices 221b as described above with reference to FIGS. 6-7. Each pair of openings 154a, 154b of the trigger wire guide 150 may be generally aligned with a corresponding aperture 227 of the proximal stent 220 of the prosthesis 200. The first and second openings 154a, 154b may be spaced longitudinally from one another such that each opening is accessible through the aperture 227. For example, the first opening 154a may be generally aligned with a distal end of the aperture 227 while the second opening 154b may be generally aligned with a proximal end of the aperture 227. The axial trigger wire 142 may be disposed within the openings 154a, 154b, as described above, such that the curve 144 extends through the aperture 227. In this example, the curve 144 may be aligned with the aperture 227 as opposed to engaging the end region 226 as described above. In other words, the end region 226 may not be disposed between the curve 144 and the trigger wire guide 150 as described above, but rather the curve 144 may be received within the aperture 227 of the proximal stent 220. The curve 144 of each axial trigger wire 142 may be disposed within the corresponding aperture 227 of the proximal stent 220 of the prosthesis 200 as shown in FIG. 11. Alternatively, the curve 144 may be disposed within any void near the proximal end of the proximal stent 220. For example, the curve 144 may be disposed within the void between two adjacent struts of the proximal stent 220.

Figure 12:
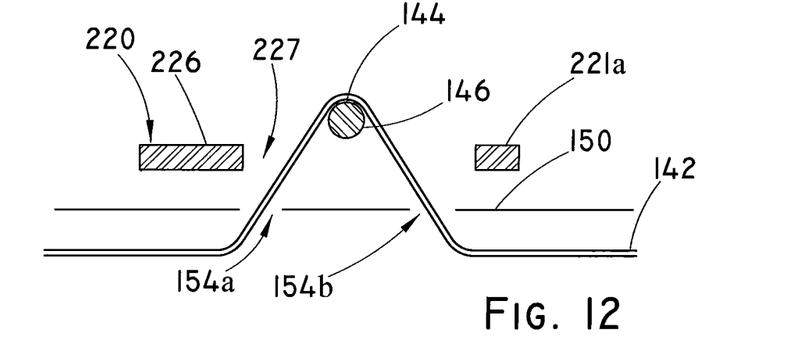
FIG. 12 is a partial longitudinal cross sectional view of the engagement between an axial trigger wire, a circumferential trigger wire, and a prosthesis as shown in FIG. 11.

The first circumferential trigger wire opening 156a may be generally aligned with a void of the proximal stent 220 so that the first circumferential trigger wire opening may be accessible through the proximal stent. For example, the first circumferential trigger wire opening 156a may be aligned with the void between two adjacent struts of the proximal stent 220. The circumferential trigger wire 146 may exit the first circumferential trigger wire opening 156a and pass through the void in the proximal stent 220. The circumferential trigger wire 146 may extend proximally and circumferentially to engage the proximal stent 220. For example, the circumferential trigger wire 146 may extend through the curve 144 of at least one of the axial trigger wires 142. FIG. 12 shows a partial longitudinal cross sectional view of one of the first proximal apices 221a engaged by a circumferential trigger wire 146 as shown in FIG. 11. The circumferential trigger wire 146 may be received within the curve 144 and between the axial trigger wire 142 and the proximal stent 220 as shown in FIGS. 11-12. The axial trigger wire 142 may engage the circumferential trigger wire 146 to retain the circumferential trigger wire in close proximity to the proximal stent 220 and the trigger wire guide 150. In other words, the axial trigger wire 142 may prevent the circumferential trigger wire 146 from moving radially away from the trigger wire guide 150. The axial trigger wire 142 also may retain the circumferential trigger wire 146 longitudinally between the distal end of the aperture 227 and the proximal end of the aperture. This may prevent the circumferential trigger wire 146 from moving proximally, and potentially slipping off of the proximal end of the proximal stent 220, or moving distally, and potentially allowing expansion of the proximal end of the proximal stent. In this manner, the proximal stent 220 may be restrained between the circumferential trigger wire 146 and the trigger wire guide 150 and in close proximity to the trigger wire guide 150.

The circumferential trigger wire 146 may extend circumferentially around at least a portion of the proximal stent 220 and the trigger wire guide 150 as shown in FIG. 11. The circumferential trigger wire 146 may be received within the curve 144 of each of the axial trigger wires 142 around the circumference of the proximal stent 220. In this manner, the circumferential trigger wire 146 may at least partially encircle an outer surface of the proximal stent 220 to restrain the proximal stent in close proximity to the trigger wire guide 150 (e.g., in the compressed configuration). The circumferential trigger wire 146 may extend proximally and reenter the trigger wire guide 150 through the second circumferential trigger wire opening 156b. The proximal end of the circumferential trigger wire 146 may be received within the nose cone dilator 116 to maintain tension on the circumferential trigger wire.

A trigger wire system having a circumferential trigger wire may be beneficial for multiple reasons. For example, the circumferential trigger wire 146 may extend circumferentially around the proximal stent 220 to engage each of the proximal apices. In other words, the circumferential trigger wire 146 may engage the first proximal apices 221a having the apertures 227 and the second proximal apices 221b having the barbs 229. Thus, the circumferential trigger wire may restrain each proximal apex of the proximal stent 220 in close proximity to the trigger wire guide 150. In this manner, the circumferential trigger wire 146 may restrain the proximal end of the proximal stent 220 in the compressed configuration.

Because the proximal stent 220 may be engaged by a single circumferential trigger wire 146 (which itself may be engaged by the axial trigger wires 142), the proximal end of the prosthesis 200 may be released by retracting the single circumferential trigger wire as opposed to multiple axial trigger wires 142. This may reduce the retraction force required to release the proximal end of the prosthesis 200. Such a reduced retraction force may provide a desirable tactile feel for a physician during deployment of the prosthesis 200 to aid in precise placement of the prosthesis within a body vessel. The ability to release the proximal end of the prosthesis 200 by retracting a single trigger wire may reduce the probability of the trigger wire becoming tangled (e.g., with other trigger wires) during deployment of the prosthesis.

The addition of the circumferential trigger wire 146 to the trigger wire system also may provide a safety factor to the deployment device 100. For example, it may become difficult or even impossible to retract the circumferential trigger wire 146 from engagement with the axial trigger wires 142. This may be caused by the circumferential trigger wire 146 snagging on a component of the prosthesis 200 or the delivery device 100 or breakage of the circumferential trigger wire. In such a situation, the axial trigger wires 142 may be retracted to release the circumferential trigger wire from engagement with the proximal stent 220. In other words, the proximal stent 220 may be released by retracting either the circumferential trigger wire 146 or the axial trigger wires 142. Providing alternative means of releasing the proximal stent 220 may enhance the safety of the deployment device 100.

The prosthesis 200 may be positioned within a body vessel of a patient using conventional endovascular techniques. Once the prosthesis 200 is in the desired location within the body vessel, the sheath 130 may be retracted to enable partial expansion of the prosthesis 200 as shown in FIG. 2. The proximal end 202 of the prosthesis 200 may be restrained in the compressed configuration by the circumferential trigger wire 146 as shown in FIG. 11. In this partially expanded configuration, the prosthesis 200 may be repositioned (e.g., rotated and/or translated) within the body vessel. Once the prosthesis 200 is positioned as desired, the proximal end 202 of the prosthesis may be released to enable expansion of the prosthesis to the expanded configuration.

The proximal end 202 of the prosthesis may be released by manipulation of the trigger wire release mechanisms. For example, the circumferential trigger wire release mechanism 123 may be unlocked and retracted distally relative to the guide wire catheter 110. Initial retraction of the circumferential trigger wire release mechanism 123 may pull the proximal end of the circumferential trigger wire 146 out of engagement with the nose cone dilator 116. Further retraction of the circumferential trigger wire release mechanism 123 may cause the circumferential trigger wire 146 to slide out of engagement with each of the axial trigger wires 142. Upon disengagement of the circumferential trigger wire 146 from the axial trigger wires 142, the proximal stent 220 of the prosthesis 200 may not be restrained by the circumferential trigger wire, and the proximal stent may expand to the expanded configuration. The circumferential trigger wire release mechanism 123 may be further retracted to remove the circumferential trigger wire 146 from the deployment device 100.

After removal of the circumferential trigger wire 146 from the deployment device 100, the axial trigger wires 142 may remain loaded in the deployment device 100 during retraction of the deployment device from the body of the patient. Alternatively, the axial trigger wires may be removed from the deployment device 100 prior to retraction of the deployment device. For example, the axial trigger wire release mechanism 121 may be unlocked and retracted distally relative to the guide wire catheter 110. Initial retraction of the axial trigger wire release mechanism 121 may pull the proximal ends of the axial trigger wires 142 out of engagement with the nose cone dilator 116. The axial trigger wire release mechanism 121 may be further retracted to slide the axial trigger wires 142 out of the openings 154a, 154b in the trigger wire guide 150 and to remove the axial trigger wires from the deployment device 100. Removing the axial trigger wires 142 from the deployment device 100 prior to retraction of the deployment device from the body of the patient may reduce the probability of catching or snagging any of the axial trigger wires on the prosthesis 200 during retraction of the deployment device.

Although the trigger wire system has been described as engaging the proximal end of the prosthesis to restrain the proximal end in the compressed configuration, the trigger wire system may engage the distal end or any other portion of the prosthesis in a similar manner to restrain the distal end or other portion of the prosthesis in the compressed configuration. In one example, one trigger wire system may engage the proximal stent of the prosthesis while another trigger wire system may engage a distal stent of the prosthesis. Alternatively, or additionally, multiple trigger wire systems may engage any portion of the prosthesis (e.g., any stent of the prosthesis) to restrain that portion in the compressed configuration.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:

1. An expandable endoluminal prosthesis and deployment device for deploying the expandable endoluminal prosthesis within a body vessel, the deployment device comprising:
    an elongate member extending longitudinally along at least a portion of a length of the deployment device;
    an expandable endoluminal prosthesis disposed about the elongate member and having an exterior circumference;
    at least one axial trigger wire coupled to the elongate member and extending outwardly from the elongate member; and
    a circumferential trigger wire extending out of a first circumferential trigger wire aperture of the elongate member, forming a single loop circumferentially around substantially the entire exterior circumference of the expandable endoluminal prosthesis and re-entering an axially spaced second circumferential trigger wire aperture in the elongate member, the single loop removably received under the axial trigger wire between the axial trigger wire and the elongate member;
    wherein the circumferential trigger wire is manipulatable from a distal end of the deployment device, whereby the circumferential trigger wire is removable from between the axial trigger wire and the elongate member.

2. The deployment device of claim 1, wherein the at least one axial trigger wire extends longitudinally along at least a portion of the length of the deployment device.

3. The deployment device of claim 2, wherein the elongate member comprises a tubular member; the axial trigger wire is received within the tubular member, exits the tubular member at a first longitudinal position, and reenters the tubular member at a second longitudinal position proximal of the first longitudinal position.

4. The deployment device of claim 3, wherein the at least one axial trigger wire comprises a plurality of axial trigger wires, the tubular member further comprises a plurality of axial trigger wire apertures, each of the plurality of axial trigger wires extends through a corresponding one of the plurality of axial trigger wire apertures.

5. The deployment device of claim 4, wherein the plurality of axial trigger wire apertures are aligned with one another with respect to a longitudinal axis of the tubular member and spaced from one another circumferentially around the tubular member.

6. The deployment device of claim 5, wherein each of the plurality of axial trigger wire apertures comprises a first aperture and a second aperture, the first and second apertures are aligned with one another with respect to a circumference of the tubular member, and the second aperture is positioned proximal of the first aperture with respect to the longitudinal axis of the tubular member.

7. The deployment device of claim 4, wherein the circumferential trigger wire extends longitudinally along at least a portion of the length of the deployment device and is removably received between each of the plurality of engagement members and an outer surface of the tubular member.

8. The deployment device of claim 1, wherein the elongate member comprises a tubular member comprising the first and second circumferential trigger wire apertures, the circumferential trigger wires are received within the tubular member, and the circumferential trigger wire extends through the first circumferential trigger wire aperture and exits the tubular member.

9. The deployment device of claim 8, wherein the first and second circumferential trigger wire apertures are aligned with one another with respect to a circumference of the tubular member, and the second aperture is positioned proximal of the first aperture with respect to a longitudinal axis of the tubular member.

10. A system comprising:
    a deployment device comprising a tubular trigger wire guide, at least one axial trigger wire aperture in the trigger wire guide, and first and second axially spaced circumferential trigger wire apertures in the trigger wire guide;
    an expandable endoluminal prosthesis positioned on the deployment device and having an exterior circumference;
    at least one axial trigger wire received within the trigger wire guide, the axial trigger wire extending through the axial trigger wire aperture and exiting the trigger wire guide; and
    a circumferential trigger wire received within the trigger wire guide, the circumferential trigger wire extending through the first circumferential trigger wire aperture and exiting the trigger wire guide and encircling the prosthesis substantially about the entire exterior circumference of the prosthesis forming a single loop and re-entering the trigger wire guide at the second circumferential trigger wire aperture, the single loop of the circumferential trigger wire passing beneath the axial trigger wire such that the circumferential trigger wire is engaged by the axial trigger wire and restrains at least a portion of the prosthesis in a compressed configuration.

11. The system of claim 10, wherein the axial trigger wire exits the trigger wire guide at a first longitudinal position and reenters the trigger wire guide at a second longitudinal position proximal of the first longitudinal position, a portion of the axial trigger wire disposed external of the trigger wire guide comprises a curve, and a portion of the circumferential trigger wire disposed external of the trigger wire guide extends circumferentially around the prosthesis and is received between the curve of the axial trigger wire and the prosthesis.

12. The system of claim 11, wherein the axial trigger wire aperture comprises a plurality of axial trigger wire apertures, the axial trigger wire comprises a plurality of axial trigger wires, each axial trigger wire extends through a corresponding one of the plurality of axial trigger wire apertures and comprises the curve, and the circumferential trigger wire is received between the curve of each of the plurality of axial trigger wires and an outer surface of the prosthesis.

13. The system of claim 10, wherein the axial trigger wire aperture comprises a plurality of axial trigger wire apertures, the prosthesis further comprises a stent comprising a plurality of end regions each including an aperture, and each aperture of the stent is aligned with a corresponding one of the plurality of axial trigger wire apertures.

14. The system of claim 13, wherein the axial trigger wire comprises a plurality of axial trigger wires, each axial trigger wire exits the trigger wire guide at a first longitudinal position and reenters the trigger wire guide at a second longitudinal position proximal of the first longitudinal position, a portion of the axial trigger wire disposed external of the trigger wire guide comprises a curve, and the curve is received within the corresponding one of the plurality of apertures of the stent.

15. The system of claim 14, wherein the plurality of end regions is a plurality of first end regions, and the prosthesis further comprises a plurality of second end regions each including a barb.

16. The system of claim 15, wherein each of the plurality of axial trigger wires is received within a corresponding one of the plurality of apertures of the stent, and the circumferential trigger wire at least partially encircles the prosthesis and engages each of the first end regions and each of the second end regions.

17. The system of claim 10, wherein the deployment device further comprises a circumferential trigger wire release mechanism, and a distal end of the circumferential trigger wire is coupled to the circumferential trigger wire release mechanism.

18. A method of deploying an expandable endoluminal prosthesis, the method comprising:
providing a deployment device comprising a tubular trigger wire guide, at least one axial trigger wire aperture in the trigger wire guide, an axial trigger wire received within the trigger wire guide and extending through the axial trigger wire aperture such that a curve of the axial trigger wire is disposed external of the trigger wire guide, a prosthesis disposed about the trigger wire guide having an exterior circumference, and a circumferential trigger wire exiting a first circumferential trigger wire aperture in the trigger wire guide, forming a single loop about substantially the entire exterior surface of the prosthesis and re-entering the trigger wire guide at an axially spaced second circumferential trigger wire aperture, the single loop passing beneath the axial trigger wire and
manipulating the circumferential trigger wire from a distal end of the deployment device, and sliding the circumferential trigger wire out of engagement between the curve of the axial trigger wire and an outer surface of the trigger wire guide.

\* \* \* \* \*